(12) United States Patent
Ray et al.

(10) Patent No.: US 12,345,680 B1
(45) Date of Patent: Jul. 1, 2025

(54) MODULAR CHEMIRESISTIVE SENSOR FOR REAL-TIME ETHYLENE MONITORING

(71) Applicant: INNOSENSE CORPORATION, Torrance, CA (US)

(72) Inventors: Anamika Ray, Torrance, CA (US); Yifan Tang, Torrance, CA (US); Tobin Gomez, Lakewood, CA (US); Jeffrey Paul, Torrance, CA (US); Mohammad Mushfiq, Los Angeles, CA (US); Maksudul Alam, Glendora, CA (US); Uma Sampathkumaran, Torrance, CA (US)

(73) Assignee: InnoSense Corporation, Torrance, CA (US)

( * ) Notice: Subject to any disclaimer, the term of this patent is extended or adjusted under 35 U.S.C. 154(b) by 965 days.

(21) Appl. No.: 17/447,416

(22) Filed: Sep. 10, 2021

Related U.S. Application Data

(63) Continuation-in-part of application No. 15/989,125, filed on May 24, 2018, now abandoned, and a continuation-in-part of application No. 15/851,587, filed on Dec. 21, 2017, now abandoned, which is a continuation-in-part of application No. 14/658,034, filed on Mar. 13, 2015, now Pat. No. 9,896,772.

(60) Provisional application No. 63/078,298, filed on Sep. 14, 2020, provisional application No. 63/077,322, filed on Sep. 11, 2020, provisional application No. 62/536,940, filed on Jul. 25, 2017, provisional application No. 61/952,557, filed on Mar. 13, 2014.

(51) Int. Cl.
*G01N 33/00* (2006.01)
*G01N 27/416* (2006.01)
*G01N 27/417* (2006.01)

(52) U.S. Cl.
CPC ....... *G01N 27/4162* (2013.01); *G01N 27/417* (2013.01); *G01N 33/0036* (2013.01)

(58) Field of Classification Search
None
See application file for complete search history.

(56) References Cited

U.S. PATENT DOCUMENTS

| | | | |
|---|---|---|---|
| 5,222,388 A | 6/1993 | Sinha | |
| 5,536,473 A | 7/1996 | Monkman | |
| 5,869,007 A | 2/1999 | Jang | |
| 6,105,416 A | 8/2000 | Nelson et al. | |
| 7,226,530 B2 | 6/2007 | Weiller et al. | |
| 7,291,503 B2 | 11/2007 | Swager | |
| 7,939,024 B2 | 5/2011 | Brongersma | |
| 7,948,041 B2 | 5/2011 | Bryant | |
| 7,956,427 B2 | 6/2011 | Lieber | |
| 8,012,326 B2 | 9/2011 | Weiller | |
| 8,030,100 B2 | 10/2011 | Besnard | |
| 8,138,005 B2 | 3/2012 | Jang | |
| 8,152,991 B2 | 4/2012 | Briman | |
| 8,178,355 B2 | 5/2012 | Acharya | |
| 8,187,865 B2 | 5/2012 | Yun | |
| 8,338,097 B2 | 12/2012 | Castro | |
| 8,394,330 B1 | 3/2013 | Lewis | |
| 8,525,237 B1 | 9/2013 | Weiss | |
| 8,668,874 B2 | 3/2014 | Tao | |
| 8,673,216 B2 | 3/2014 | Chen et al. | |
| 8,683,672 B2 | 4/2014 | Deshusses et al. | |
| 8,703,500 B2 | 4/2014 | Zang | |
| 8,951,473 B2 | 2/2015 | Wang et al. | |
| 8,961,880 B2 | 2/2015 | Virji | |
| 9,739,737 B2 | 8/2017 | Swager et al. | |
| 2004/0192072 A1 | 9/2004 | Snow et al. | |
| 2004/0241164 A1 | 12/2004 | Bales | |
| 2004/0241436 A1 | 12/2004 | Hsieh | |
| 2005/0036905 A1 | 2/2005 | Gokturk | |
| 2005/0072213 A1 | 4/2005 | Besnard et al. | |
| 2005/0129573 A1 | 6/2005 | Gabriel | |
| 2005/0212531 A1 | 9/2005 | Wei | |
| 2006/0194263 A1 | 8/2006 | Boussaad et al. | |
| 2006/0207878 A1 | 9/2006 | Myung et al. | |
| 2007/0114138 A1 | 5/2007 | Krasteva | |
| 2007/0269900 A1 | 11/2007 | Lebret | |
| 2007/0281362 A1 | 12/2007 | Vink | |
| 2007/0295203 A1* | 12/2007 | Shekarriz | G01N 27/4162 204/431 |

(Continued)

OTHER PUBLICATIONS

Innam Lee, Xiliang Luo, Xinyan Tracy Cui, and Minhee Yuna, "Highly Sensitive Single Polyaniline Nanowire Biosensor for the Detection of Immunoglobulin G and Myoglobin", Biosens Bioelectron, 26(7), pp3297-3302 (Mar. 15, 2011).

Cristescu SM, De Martinis D, Hekkert ST, Parker DH, Harren FJM. "Ethylene Production By Botrytis Cinerea In Vitro and in Tomatoes", *Applied and Environmental Microbiology*, 2002, 68: pp. 5342-5350.

Schroder R, Cristescu SM, Harren FJ, Hilker M., "Reduction of Ethylene Emission From Scots Pine Elicited by Insect Egg Secretion.", *Journal of Experimental Botany*, 2007. 58: pp. 1835-1842.

Tuomainen J, Betz C, Kangasjarvi J, Ernst Yin Z-H, Langebartels C, Sandermann H. "Ozone Induction of Ethylene Emission in Tomato Plants: Regulation by Differential Accumulation of Transcripts for the Biosynthetic Enzymes", *The Plant Journal*, 1997, 12, pp. 1151-1162.

(Continued)

*Primary Examiner* — Christopher M Gross
(74) *Attorney, Agent, or Firm* — Polson Intellectual Property Law P.C.; Margaret Polson

(57) ABSTRACT

A system for sensing the presence and concentration of ethylene in a gas stream includes an ethylene sensor, an ethylene scrubber, a $CO_2$ scrubber, gas flow control valves, a pump, and electrical components to receive and analyze the electrical signals generated by the ethylene sensor as the ethylene concentration in the gas stream changes. The system, in a controlled manner, alternatively feeds quantities of the gas stream being analyzed to the ethylene sensor or through scrubber components of the system. The ethylene sensor comprises conductive polymeric nanofibers functionalized to detect the presence of ethylene and generate an electrical signal that changes as the ethylene concentration changes.

6 Claims, 16 Drawing Sheets

(56) References Cited

U.S. PATENT DOCUMENTS

| | | |
|---|---|---|
| 2009/0275143 A1 | 11/2009 | Misra |
| 2009/0294303 A1 | 12/2009 | Fischer |
| 2010/0000883 A1 | 1/2010 | Morrin |
| 2010/0005858 A1 | 1/2010 | Virji |
| 2010/0089772 A1 | 4/2010 | Deshusses |
| 2010/0112546 A1 | 5/2010 | Lieber et al. |
| 2010/0273665 A1 | 10/2010 | Haick |
| 2010/0282245 A1 | 11/2010 | Star |
| 2010/0325073 A1 | 12/2010 | Haick |
| 2011/0171629 A1 | 7/2011 | Swager et al. |
| 2011/0287551 A1 | 11/2011 | Weiller |
| 2011/0300637 A1 | 12/2011 | Virji |
| 2012/0097917 A1 | 4/2012 | Zhou et al. |
| 2012/0134880 A1 | 5/2012 | Kurkina |
| 2012/0298530 A1 | 11/2012 | Yunus |
| 2013/0034910 A1 | 2/2013 | Haick |
| 2013/0040397 A1 | 2/2013 | Star |
| 2013/0115705 A1 | 5/2013 | Patolsky |
| 2013/0209991 A1 | 8/2013 | Wang |
| 2014/0021067 A1 | 1/2014 | Samuilov |
| 2014/0154785 A1 | 6/2014 | Yun |
| 2015/0008486 A1 | 1/2015 | Bryant |
| 2015/0056471 A1 | 2/2015 | Joo |
| 2015/0204860 A1 | 7/2015 | Chui |
| 2016/0178567 A1 | 6/2016 | Lee et al. |
| 2018/0088117 A1 | 3/2018 | Panchapakesan et al. |

OTHER PUBLICATIONS

Dhawan KR, Bassi PK, Spencer MS. "Effects of Carbon-Dioxide on Ethylene Production and Action in Intact Sunflower Plants", *Plant Physiology*, 1981, 68, pp. 831-834.

Vergara R, Parada F, Rubio S, Perez FJ. "Hypoxia Induces H2O2 Production and Activates Antioxidant Defense System in Grapevine Buds Through Mediation of H2O2 and Ethylene.", *Journal of Experimental Botany*, 2012. 63(11), pp. 123-131.

Thain SC, Vandenbussche F, Laarhoven LJJ. "Circadian Rhythms of Ethylene Emission in Arabidopsis", Plant Physiology, 2004. 136, pp. 3751-3761.

Orihuel-Iranzo B, Miranda M, Zacarias L, Lafuente MT. Temperature and Ultra Low Oxygen Effects and Involvement of Ethylene in Chilling Injury of 'Rojo Brillante' Persimmon Fruit, Food Science Technology International, 2010, 16, pp. 159-167.

Hermans C, Vuylsteke M,Coppens F, Craciun A, Inze D, Verbruggen N., "Early Transcriptomic Changes Induced by Magnesium Deficiency in *Arabidopsis Thaliana* Reveal the Alteration of Circadian Clock Gene Expression in Roots and the Triggering of Abscisic Acid-Responsive Genes", New Phytologist, 2010, 187, pp. 119-131.

Janssen S. Schmitt K., Blanke M., Bauersfeld M.L. Ethylene detection in fruit supply chains, Philos Trans A Math Phys Eng Sci, 2014, Jun. 13; 372(2017): 20130311).

Zheng et al. Multiplexed electrical detection of cancer markers with nanowire sensor arrays, Oct. 2005, Nature Biotechnology, vol. 23, No. 10.

Cella et al. Single-Walled Carbon Nanotube-Based Chemiresistive Affinity Biosensors for Small Molecules: Ultrasensitive Glucose Detection, JACS, vol. 132, pp. 5024-5026. (Year: 2010).

Yang et al. Fabrication of Single-Walled Carbon Nanotubes (SWNTs) Field-Effect Transistor (FET) Biosensor, 2010 3rd International Conference of Biomedical Engineering and Informatics, pp. 1482-1485 (Year: 2010).

Lacey et al. How Plants Sense Ethylene Gas—The Ethylene Receptors, Journal of Inorganic Biochemistry, 133 (2014) pp. 58-63.

* cited by examiner

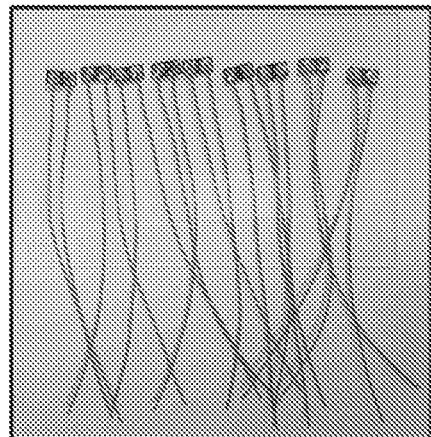 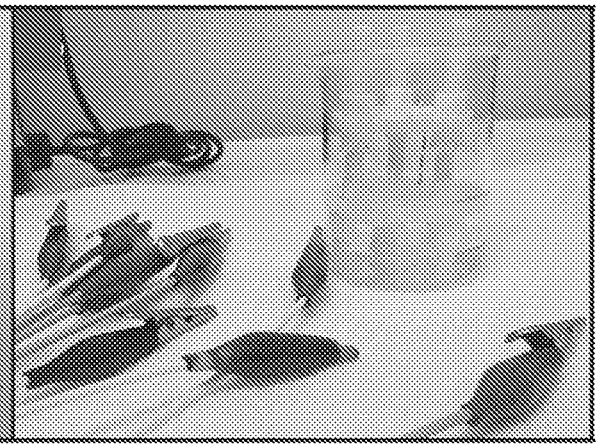
FIGURE 13A  FIGURE 13B
 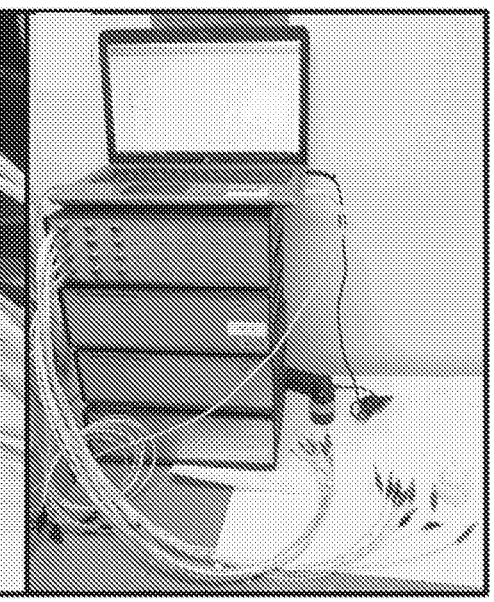
FIGURE 13C  FIGURE 13D

| Elemental Analysis Theoretical % | | | Elemental Analysis Actual % | | |
|---|---|---|---|---|---|
| C % | H % | N % | C % | H % | N % |
| 27.21 | 0.91 | 12.69 | 28.40 | 1.22 | 13.71 |

MODULAR CHEMIRESISTIVE SENSOR FOR REAL-TIME ETHYLENE MONITORING

This application claims priority based on U.S. Application No. 63/077,322 filed Sep. 11, 2020 and U.S. Application No. 63/078,298 filed Sep. 14, 2020 and is Continuation-in-Part of U.S. patent application Ser. No. 15/989,125 filed May 24, 2018 claiming benefit of U.S. Application 62/536,940 filed Jul. 25, 2017 and is a Continuation-in-Part of U.S. patent application Ser. No. 15/851,587 filed Dec. 21, 2017 which is a Continuation-in-Part of U.S. patent application Ser. No. 14/658,034, filed Mar. 13, 2015 and issued as U.S. Pat. No. 9,896,772, which claims priority based on U.S. Patent Application No. 61/952,557, filed Mar. 13, 2014, all of which are incorporated herein in their entirety by reference.

Inventions described herein were made with government support under National Aeronautics and Space Administration (NASA Award Nos. NNX16CK12P and NNX17CK03C). The US Government may have certain rights in the inventions described herein.

FIELD OF THE INVENTION

The present invention, and the above referenced applications, relates to a modular chemiresistive sensor incorporating conductive polymeric nanowires or carbon nanotubes and devices using and/or incorporating these sensors. In particular, these devices include, but are not limited to modular chemiresistive sensors for hypergolic fuel and oxidizer leak detection, carbon dioxide and ethylene monitoring and detection of specific disease biomarkers. Various embodiments include biosensor platforms comprising microelectronic devices which use conductive polymeric fibers or single walled carbon nanotubes (SWNT) as the active sensing materials. The fibers or carbon nanotubes can then be further functionalized with biomarkers, such as antibodies or capture molecules, such as peptide ligands, that detect specific antigens or engineered DNA, RNA, aptamers, or engineered miRNAs and their variants that detect corresponding complementary engineered and recombinant molecules or structures either individually or in combination. Multiple devices with different biomarkers can be used in tandem to provide a diagnosis matrix for more precise and accurate results on targeted disease or biological process monitoring.

Disclosed herein is an ethylene monitoring platform comprising microelectronic devices which use conductive nanowires, for example polyaniline (PANI) nanowires, as the active sensing materials that are further functionalized with Copper(I) ($Cu^I$) and/or Copper(II) ($Cu^{II}$) and/or antibodies, peptide ligands or aptamers. Peptide ligands and/or aptamers as capture molecules to ethylene receptor complexes and their isoforms can result in partially reversible signal output while the cooper (II) complex results in reversible signal output. Described herein is a sensor system which includes scrubbers for removing interfering metabolites, including but not limited to $CO_2$, ethanol, and acetaldehyde, the presence of which, if not removed, can result in erroneous determinations of ethylene concentrations.

The sensor described herein are used in an in vitro system using engineered sequences that correspond to the ethylene receptors in various combinations to detect ethylene. When the aptamers and/or peptide ligands are synthesized to correspond to the various ethylene receptors, they are also engineered to attach to the nanowires with amino modification or various other modifications. Various different peptide ligands and/or aptamers described in the literature are suitable for functionalizing the conductive polymer nanowires used to bridge the cap between the conductive electrodes comprising the sensor and for detecting and monitoring the presence and concentrations of ethylene. See for example Innam Lee, Xiliang Luo, Xinyan Tracy Cui, and Minhee Yuna, "Highly Sensitive Single Polyaniline Nanowire Biosensor For The Detection Of Immunoglobulin G And Myoglobin", *Biosens Bioelectron.* 26(7), pp 3297-3302 (Mar. 15, 2011).

BACKGROUND

Ethylene ($C_2H_4$), a natural metabolite in plants, is a non-polar, gaseous small molecule that acts as a useful indicator of fruit ripeness. In plant growth systems, where ethylene diffuses freely, monitoring ethylene in the plant system environment can act as a useful way to determine fruit ripeness. Ethylene concentration from 5 to 10 parts per million (ppm) affect the chlorophyll in the peel without penetrating the fruit. However, higher concentrations of 10-15 ppm result in peel breakage, which can accelerate spoilage (U.S. Pat. No. 6,105,416, issued Aug. 22, 2000; Nelson B N, Richard II V R, Kane J A. "Ethylene monitoring and control system.") When this happens, the entire batch is discarded.

On the other hand, ethylene below about 5 ppm will delay the degreening process. Endogenous ethylene production is influenced by biotic factors such as pathogen attack and herbivorous predation (Cristescu S M, De Martinis D, Hekkert S T, Parker D H, Harren F J M. "Ethylene Production By *Botrytis Cinerea* In Vitro And In Tomatoes". Applied and Environmental Microbiology. 2002. 68: pp. 5342-5350; Schroder R, Cristescu S M, Harren F J, Hilker M., "Reduction Of Ethylene Emission From Scots Pine Elicited By Insect Egg Secretion.", *Journal of Experimental Botany.* 2007. 58: pp. 1835-1842.).

Ethylene production can also be influenced by abiotic environmental factors such as a) chemical exposure (Tuomainen J, Betz C, Kangasjarvi J, Ernst Yin Z-H, Langebartels C, Sandermann H. "Ozone Induction Of Ethylene Emission In Tomato Plants: Regulation By Differential Accumulation Of Transcripts For The Biosynthetic Enzymes", *The Plant Journal.* 1997, 12, pp. 1151-1162.), b) oxygen ($O_2$), or carbon dioxide ($CO_2$) levels (Dhawan K R, Bassi P K, Spencer M S. "Effects Of Carbon-Dioxide On Ethylene Production And Action In Intact Sunflower Plants", *Plant Physiology.* 1981, 68, pp. 831-834., Vergara R, Parada F, Rubio S, Perez F J. "Hypoxia Induces $H_2O_2$ Production And Activates Antioxidant Defense System In Grapevine Buds Through Mediation Of $H_2O_2$ And Ethylene.", *Journal of Experimental Botany.* 2012. 63(11), pp. 123-31.), c) day-length, light-intensity (Thain S C, Vandenbussche F, Laarhoven L J J. "Circadian Rhythms Of Ethylene Emission In *Arabidopsis*". *Plant Physiology.* 2004. 136, pp. 3751-3761.), d) and temperature or nutrient availability (Orihuel-Iranzo B, Miranda M, Zacarias L, Lafuente M T. Temperature And Ultra LowOxygen Effects And Involvement Of Ethylene In Chilling Injury Of 'Rojo Brillante' Persimmon Fruit", *Food Science Technology International.* 2010, 16; pp. 159-167, Hermans C, Vuylsteke M, Coppens F, Craciun A, Inze D, Verbruggen N., "Early Transcriptomic Changes Induced By Magnesium Deficiency In *Arabidopsis Thaliana* Reveal The Alteration Of Circadian Clock Gene Expression In Roots And The Triggering Of Abscisic Acid-Responsive Genes", *New Phytologist.* 2010.187, pp. 119-131.).

Also, ethylene emissions may depend on the plant species, organ type (e.g., flower, root, or leaf) and developmental stage of the plant. Efficient and automated in situ measurements of ethylene would greatly enable efficient fruit and crop management resulting in minimal food spoilage, waste, and controlled ripening.

An ethylene analyzer for monitoring the ripening of fruits and vegetables needs to provide real-time in situ measurements to enable informed and appropriate mitigation of the ripening process and timely harvesting of the ripening produce at an appropriate time. Moreover, the analyzer for such applications need to operate in the presence of interfering metabolites such as carbon dioxide, ethanol, acetaldehyde and $CO_2$. A problem with current ethylene analyzers is the lack of portable units that can detect ethylene at a resolution of a few ppb. Most ethylene analyzers are suitable for lab settings such as gas chromatography (GC) or near-infrared methods due to lack of sensitivity, size, operational constraints, and costs. Detection using currently available electrochemical instruments is sensitive to interfering gases, has a limited temperature range and requires shut down for periodic maintenance.

Photoacoustics is another option but is expensive and has limited selectivity in the presence of interfering gases (Janssen S. Schmitt K., Blanke M., Bauersfeld M. L. Ethylene detection in fruit supply chains, *Philos Trans A Math Phys Eng Sci.* 2014 Jun. 13; 372(2017): 20130311).

There is a clear economic incentive to monitor fruits to maintain their freshness, flavor, and shelf-life and to minimize waste due to spoilage and overripening. A compact, sensitive, and selective in situ ethylene analyzer such as described herein provides quantitative measurements of ethylene concentrations during growth and storage in large industrial warehouses and under cold storage. In addition to applications in the agricultural industry, there is a need for ethylene monitoring in autonomously operating spacecraft with a quasi-self-sustained system where plants would be grown to provide fresh food, oxygen and remove $CO_2$ such as NASA programs and independent commercial interplanetary space exploration programs. In a resource-limited environment and long-term space missions reducing waste is not just a financial issue, it is critical to mission success and the health of the occupants of the spacecraft.

SUMMARY

The present embodiments relate to a modular chemiresistive sensor. In particular, a modular chemiresistive sensor for detecting leaks of stored chemicals, particularly hypergolic fuel and oxidizer leak detection, carbon dioxide and ethylene monitoring and detection of disease biomarkers. The sensor has two conductive electrodes, preferably two gold or platinum electrodes, mounted on a silicon substrate. The electrodes are connected to a power source and are separated by a gap of 0.5 to 4.0 µm. Electrically conductive polymer nanowires or carbon nanotubes are grown or deposited in the gap between the electrodes, providing a conductive path between the electrodes. The nanowires and nanotubes are functionalized with receptor complexes for providing sensors responsive to concentrations of target compounds. A panel of biomarkers can be used for disease detection, a Copper(I) complex containing fluorinated trix (pyrazolyl)borate ligand or other copper complexes such as copper (I) trifluoromethane sulphonate benzene complex and 2-(1-hydroxyethylidene)-1-cyclopentanone copper (II) can be used for detecting certain chemical compounds, and engineered peptide ligands and/or aptamers sensitive to specific gaseous compounds, such as ethylene, can be used to functionalize the nanowires or nanotubes.

The functionalized nanowires/nanotubes form an electrically conductive nano-network spanning the gap between the electrodes. The electrodes are also connected to a circuit board having a processor and data storage for comparison of the electrical characteristics with pre-established electrical characteristic of the compound being detected and monitored. Changes in various electrical characteristics, such as current, resistance, and/or voltage values resulting from exposure of the nano-network are measured and those values are compared with data stored in the data storage portion of the detection system assigned to the target compound so that their concentrations can be determined.

BRIEF DESCRIPTION OF DRAWING

FIGS. 9A and 9B are schematic diagrams of the measurement and scrubbing cycles of the device illustrated in FIG. 8 wherein FIG. 9B shows a measurement cycle and FIG. 9A illustrates a scrub cycle.

FIG. 13A shows microelectrode devices prepared for nanowire growth.

FIG. 13B shows multiplexer devices with leads (24) from a first instrument (CH Instruments, Austin, TX; hereinafter "CHI instrument").

FIG. 13C shows devices connected to the leads of the CHI instrument and ready for growth.

FIG. 13D is a view of the CHI instruments with 8, 24 channels, controlling a computer contain a software program for controlling the electropolymerization process.

DETAILED DESCRIPTION

Ethylene Monitoring

Figure 1:
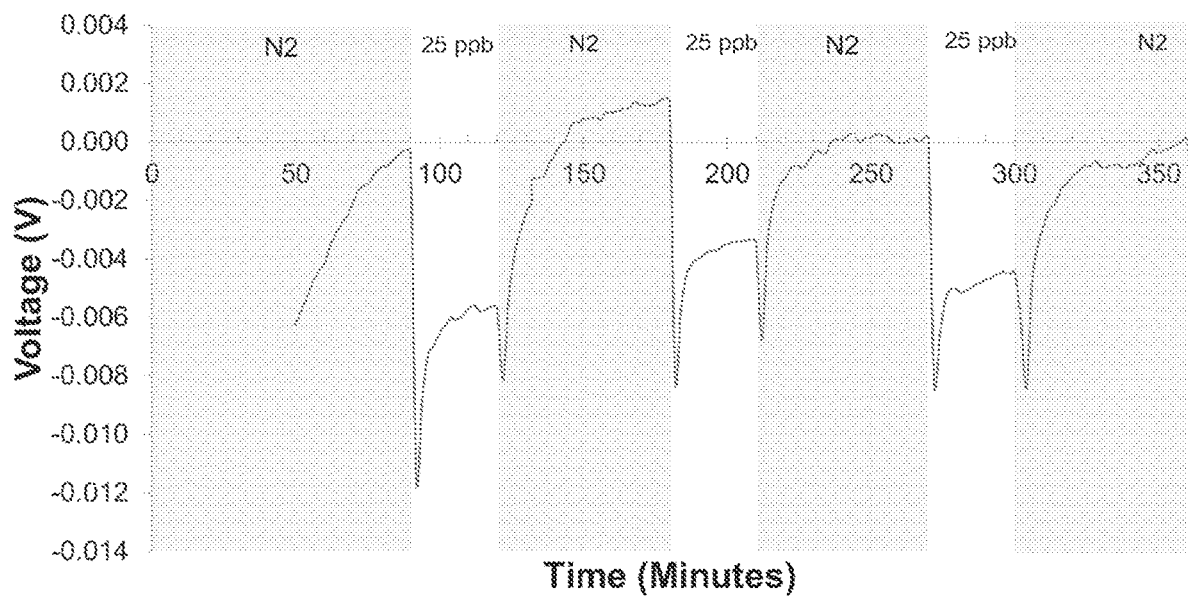
FIG. 1 is a graph generated using a device as described herein of a test conducted to determine response to 25 ppb ethylene in a nitrogen ($N_2$) atmosphere showing voltage reading as a function of time.
Figure 2:
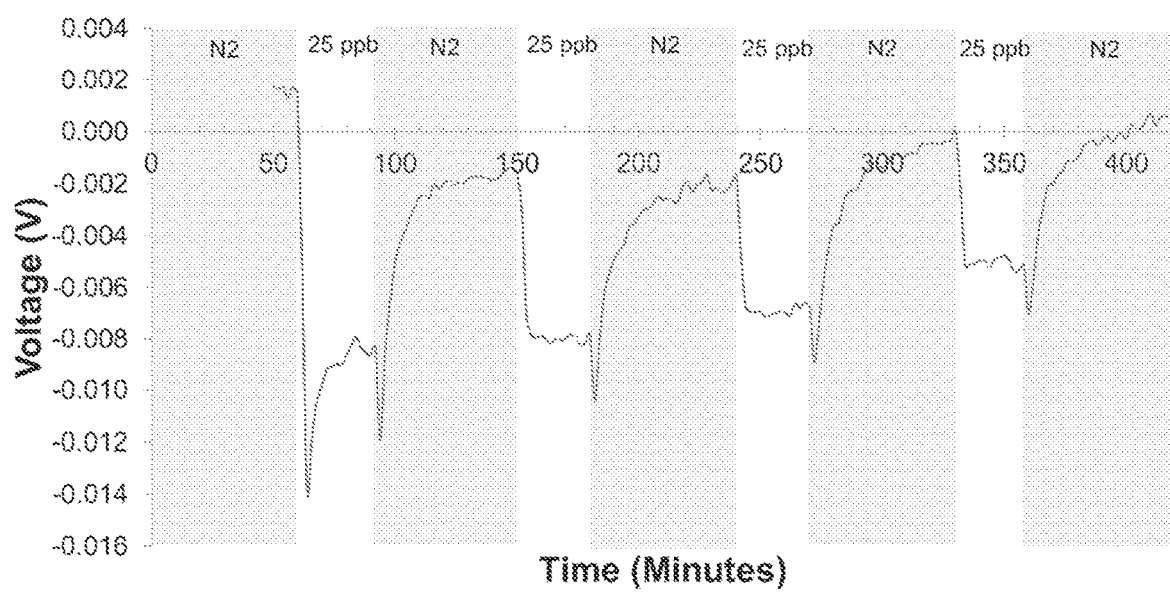
FIG. 2 is a graph showing a second response curve generated by the device in response to 25 ppb ethylene.
Figure 3:
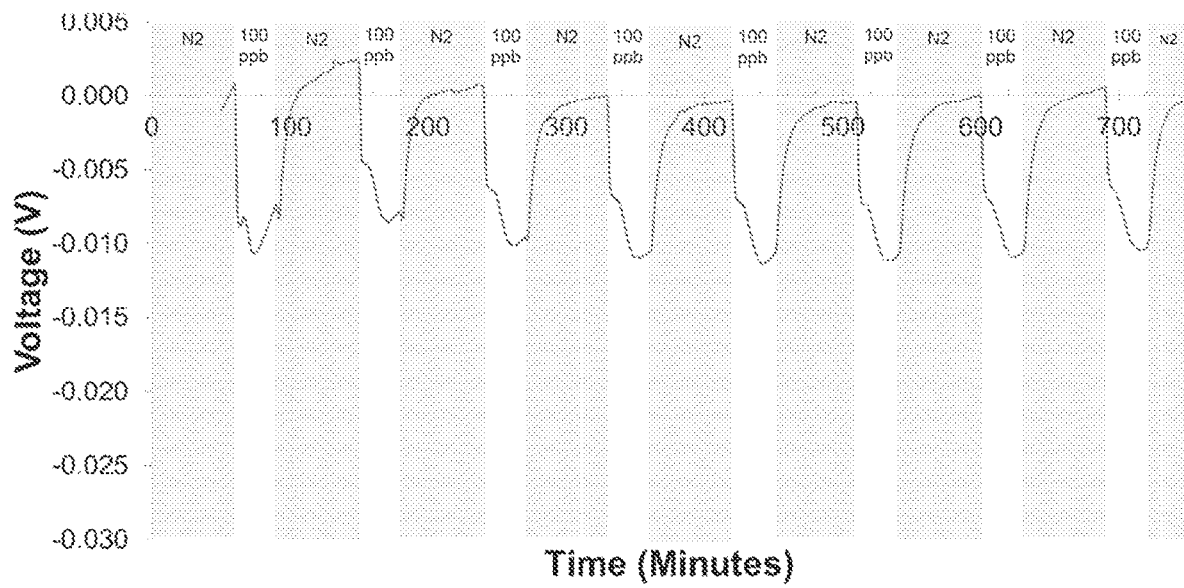
FIG. 3 is a graph showing response of the device to 100 ppb following storage of the device under vacuum for 6 months.
Figure 4:
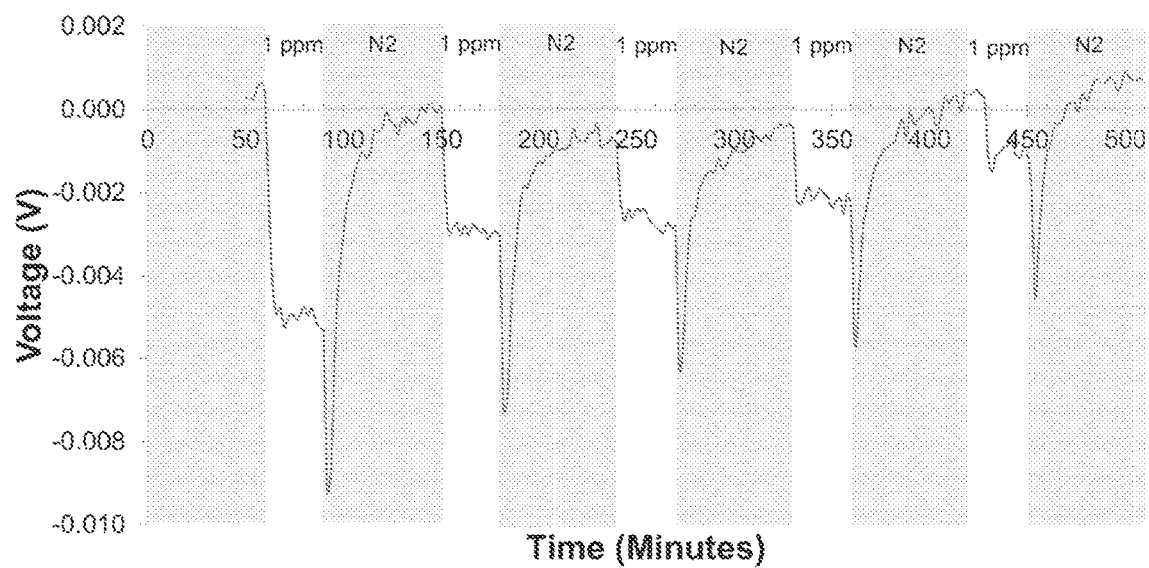
FIG. 4 is a graph showing the response of a described device to 1 ppm ethylene.
Figure 5:
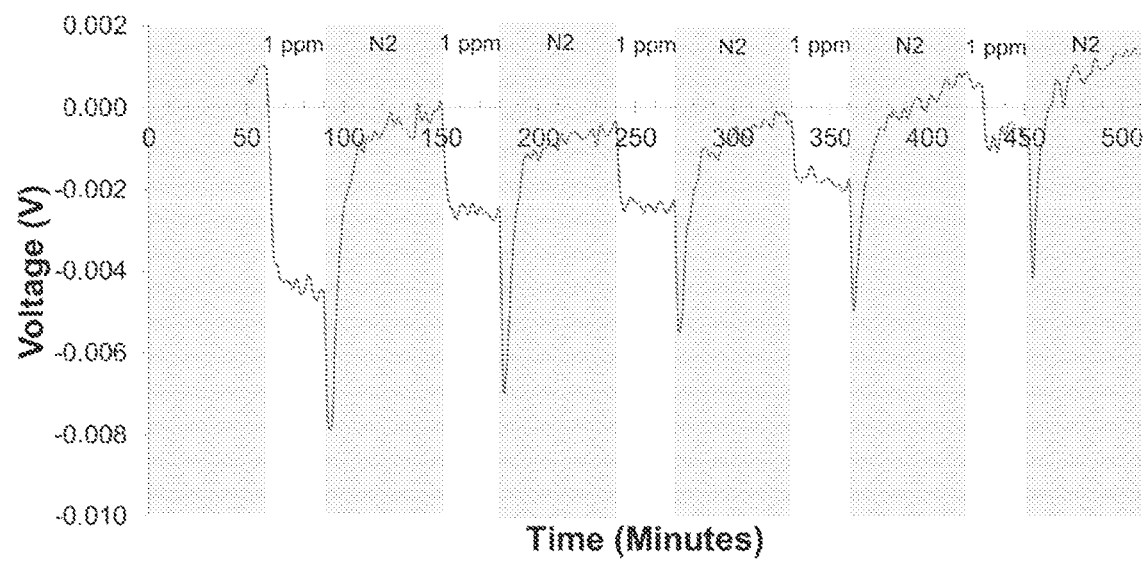
FIG. 5 is a second graph showing a device response to 1 ppm ethylene.
Figure 6:
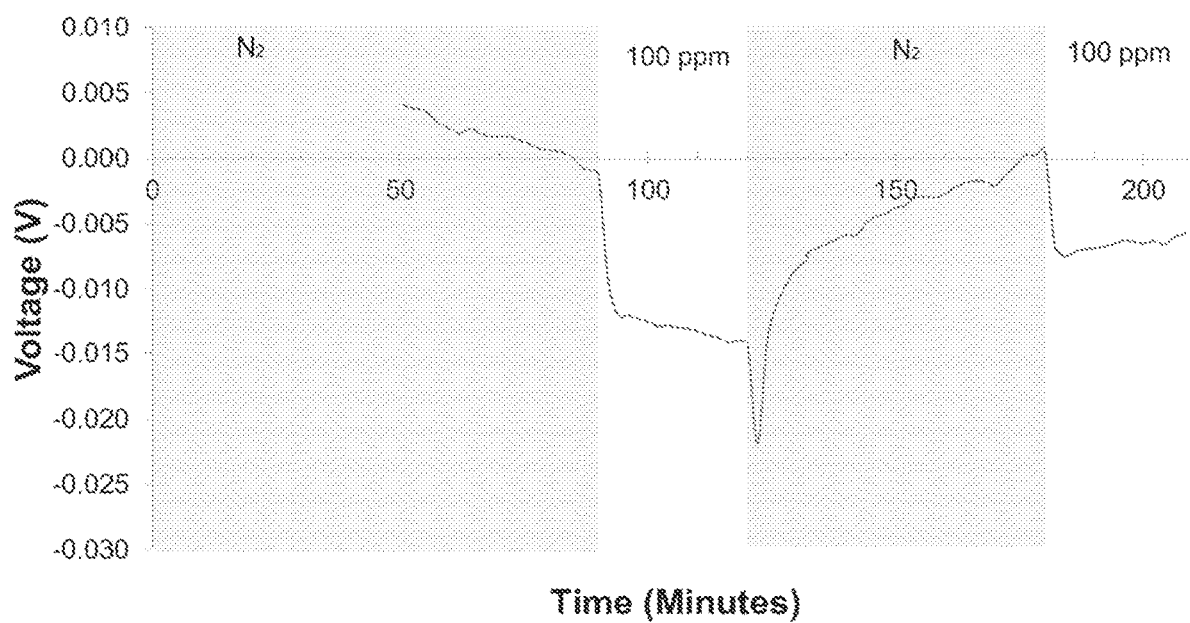
FIG. 6 is a graph showing a single cycle of $N_2$ vs 100 ppm ethylene exposure.
Figure 7:
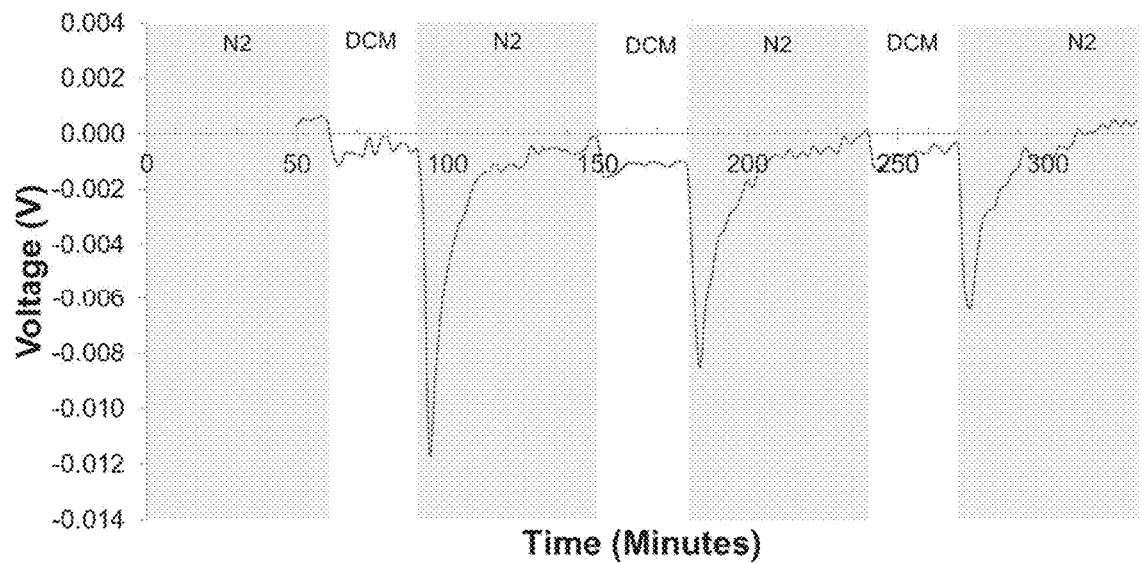
FIG. 7 is a graph showing that the ethylene sensor is not sensitive to dichloromethane, a common gas often present in parts per million concentrations in the ethylene containing atmosphere.
Figure 8:
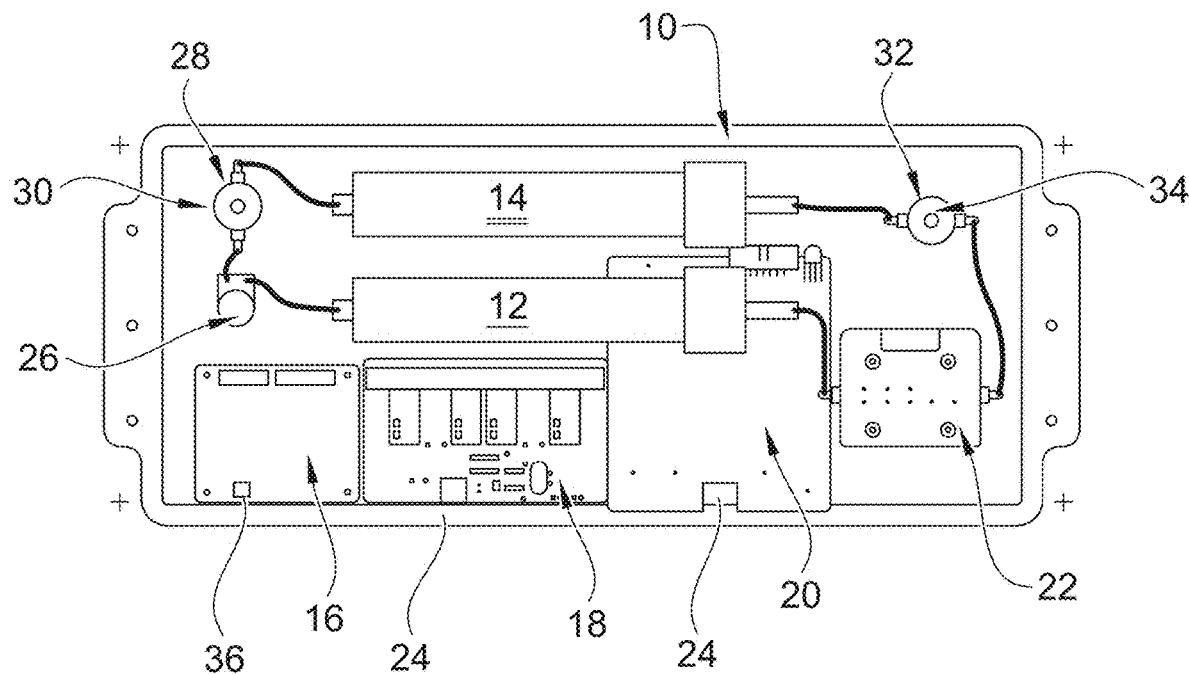
FIG. 8 is a diagram showing the components of the device incorporating features of the invention used to generate the data illustrated in the graphs of FIGS. 1-7.
Figure 9A:
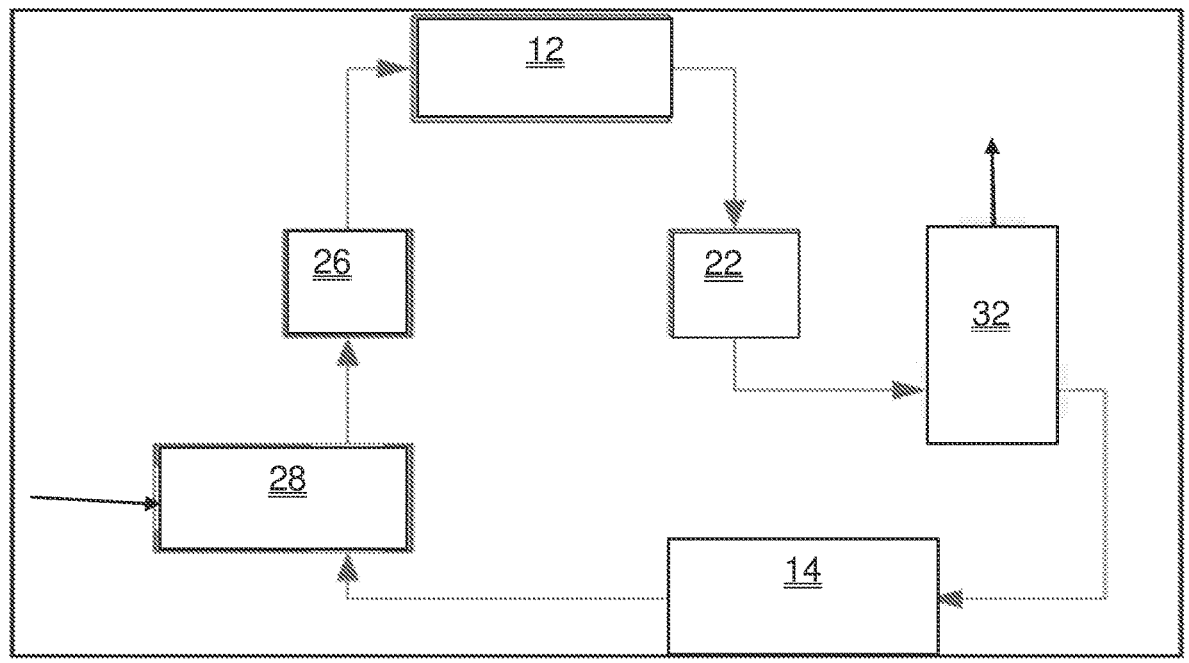
Figure 9B:
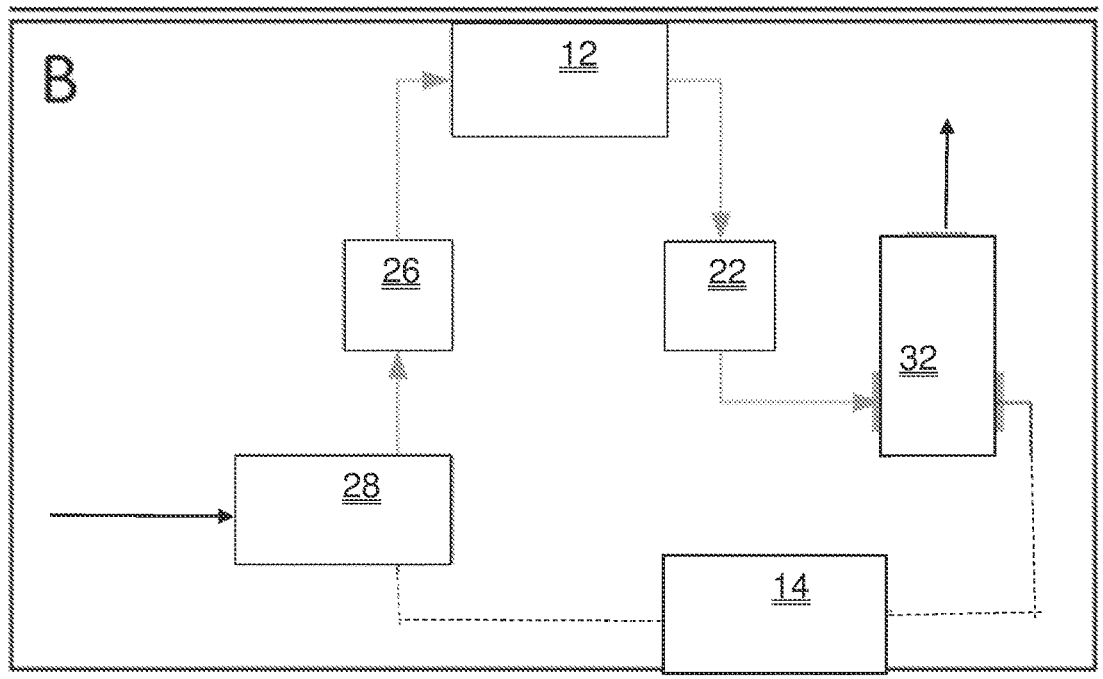

By formation of a nano-network of conductive polymer nanowires and functionalization of that nano-network with materials such as described herein, ethylene nanowire sensors and a system as shown in FIGS. 8, 9A and 9B for monitoring ethylene in the presence of interfering metabolites has been developed. The customized nanowire sensors detect ethylene reversibly with a dynamic range of from 25 ppb to 100 ppm of ethylene (FIG. 1-6). Note that the time values in minutes for FIGS. 1-7 are shown in each graph below the vertical line representing 0.000 voltage. Using a DC intensity measurement system and the scrubbing system described and shown in the FIG. 8 herein, ethylene concentrations as low as 20 ppb were detected and measured. FIGS. 1 and 2 are graphs generated for ethylene concentrations of 25 ppb where the functionalized nanowire sensors selectively responded to ethylene in the presence of various different interfering metabolites. FIG. 3 is a graph generated for ethylene concentrations of 100 ppb. FIGS. 4 and 5 are graphs generated for ethylene concentrations of 1 ppm. FIG. 6 is a graph generated for ethylene concentrations of 100 ppm. FIG. 7 is a similar graph generated for dichloromethane.

One example of the sensor housing 10, which has dimensions of 14"×6"×3.5", comprises a chemical analysis section and an electronics section as shown in FIG. 8. FIGS. 9A and 9B are drawings illustrating the operational cycles schematically.

Sensor Housing

FIG. 8 illustrates of the components of the chemical sensing system 10 which consists of a chemical analysis section and an electronics section.

The electronics section comprising the power supply board 16, the control board 18, and the measurement board 20. The power supply board 16 includes a connection 36 for receiving power from an external source. In a preferred embodiment power to the system 10 is provided by a 28 VDC external voltage source (not shown). However, the system 10 can be configured to receive an AC input or a different DC voltage. The power supply board 16 generates a 3.3 VDC voltage for operating the system pump 26. The power supply board 16 also provides power to operate two control valves (inlet valve 28 which controls the inlet port 30 and exhaust valve 32 which controls the exhaust port 34). The control board 18 includes electromechanical relays that control the operation of the valves 28, 32 and pump 26. The control board 18 and measurement board 20 board each have a USB interface 24 that connects to a computer (not shown) that runs the software for operating the system 10. The measurement board has components configured to read the resistance of the nanowire sensor chips and transmit the data to the computer through a separate USB interface 24 on the measurement board.

The chemical analysis section comprises the sensor cell 22, the inlet and exhaust valves 28, 32, the ethylene scrubber 14 and the $CO_2$ scrubber 12, and the pump 26 that controls the flow through the sensor cell 22 of the gas being tested.

The system 10 has two operational cycles for the flow of gas through the system; a measurement cycle shown in FIG. 9B and a scrubbing cycle shown in FIG. 9A. In the measurement cycle, as shown by the arrows in FIG. 9B, the gas flows from chamber (not shown) being monitored, such as a plant growth chamber, into the system 10 through a small inlet tube attached to the inlet port 30 on the inlet valve 28. The pump 26 then delivers the gas through the $CO_2$ scrubber 12 and then into the sensor cell 22, which is a sealed flow cell with up to five individual sensor chips. Gas then exits the sensor cell 22 through the exhaust port 34 on the exhaust valve 32 and is exhausted out of the system 10. The $CO_2$ scrubber 12 is a unit designed to remove $CO_2$ from the gas stream being sampled without absorbing ethylene from that gas stream.

When the measurement cycle (FIG. 9B) is completed, the system enters the recovery cycle (FIG. 9A) in which the inlet and exhaust valves 28, 32 are switch so that once a gas stream enters the system the gas flows continuously in a closed loop manner over the sensor cell 22 and through both the $CO_2$ scrubber 12 and ethylene scrubber 14 while the electrical resistance of the sensors in the sensor cell 22 are monitored by the measurement board 18. The recovery cycle continues until the sensors are fully recovered as evidenced by the sensor outputs being returned to their resting (base line) status at which time the circulating gas stream is exhausted through exhaust valve 32. The measurement cycle is then resumed.

Polymer Nanowire Growth

Figure 21:
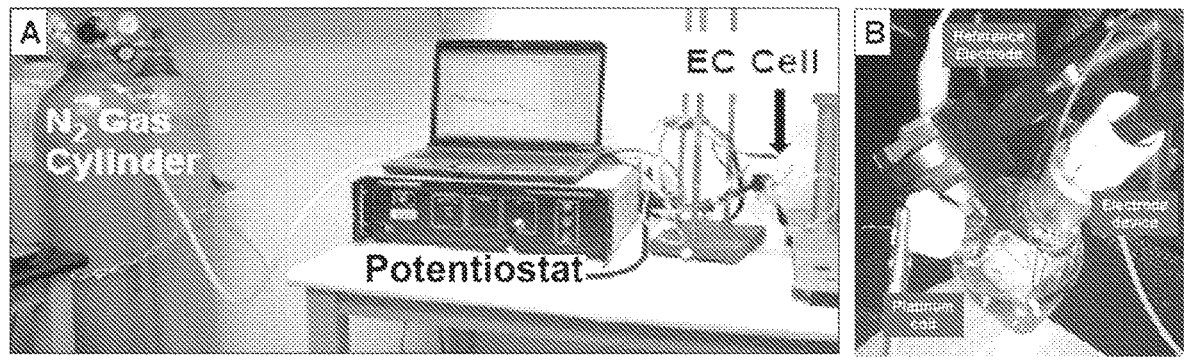
FIG. 21 is a copy of FIG. 1 appearing in parent U.S. Pat. No. 9,896,772.
Figure 22:
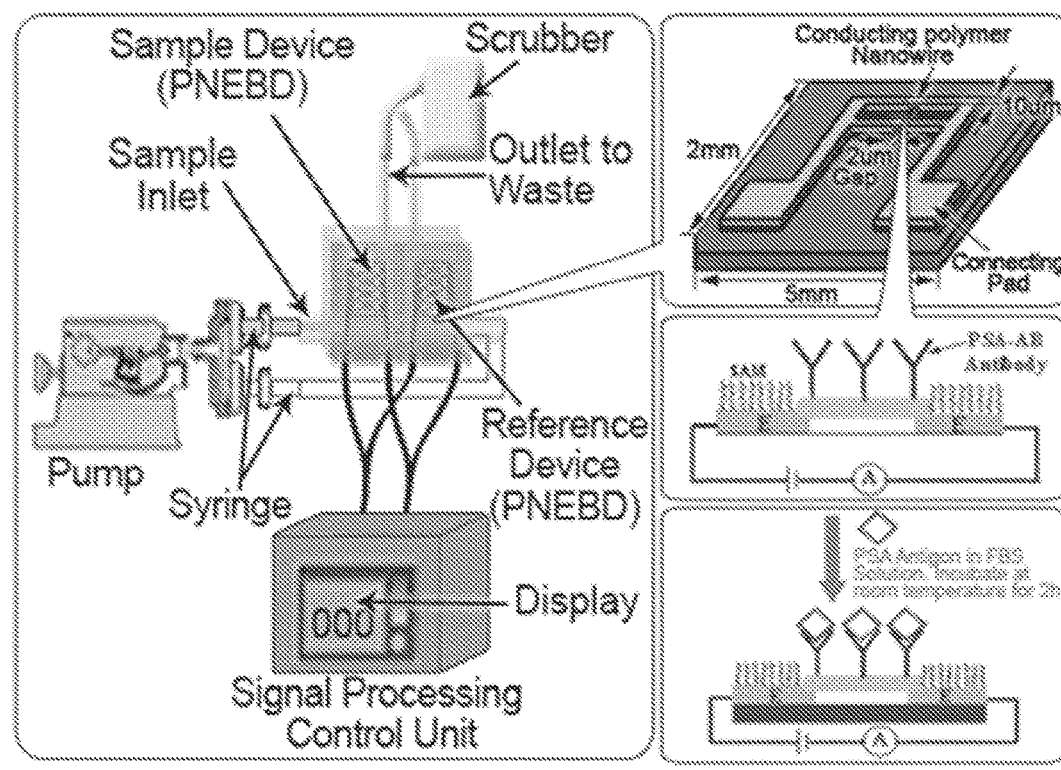
FIG. 22 is a copy of FIG. 21 appearing in parent U.S. Pat. No. 9,896,772.

Prior to the polymer nanowire growth, the devices are cleaned and activated. The electro-polymerization set up for growth of polymer nanowires is shown and described in parent application, issued as U.S. Pat. No. 9,896,772, particularly FIGS. 1 and 21 therein, incorporated herein in their entirety by reference and reproduced as FIGS. 21 and 22 herein. The electrochemical process uses a small volume electrochemistry cell/flask containing ~18 mL of 0.1M to 0.5M monomer solution selected to obtain the preferred density of the nanowires formed. A wire-bonded electrode junction device is submerged in 0.1 M aniline in 0.8 M nitric acid. One side of the wire bonded device functions as the working electrode while a silver/silver chloride (Ag/AgCl)

electrode is used as a reference electrode. A platinum (Pt) coil preferably having 10-12 turns of a Pt wire having a diameter of 0.25 mm, is used as the counter electrode. To remove any air from the electro-polymerization system, the solution was purged with $N_2$ for ten minutes prior to starting the electrochemical reaction. A $N_2$ atmosphere was also constantly maintained in the electrochemical flask to keep a neutral environment above the solution and prevent oxidation. An oxidative potential was applied to one side of the electrode junction device and grounded to the platinum coil. To generate the potential difference for the electrochemical reaction, a potentiostat (Princeton Applied Research model 263A-1 potentiostat/galvanostat) and a CHI instrument were used as shown in FIG. 1 of U.S. Pat. No. 9,896,772 included herein as FIG. 21. This method oxidizes the monomers and triggers a chain reaction resulting in the formation of polymer nanowires.

Figure 10:
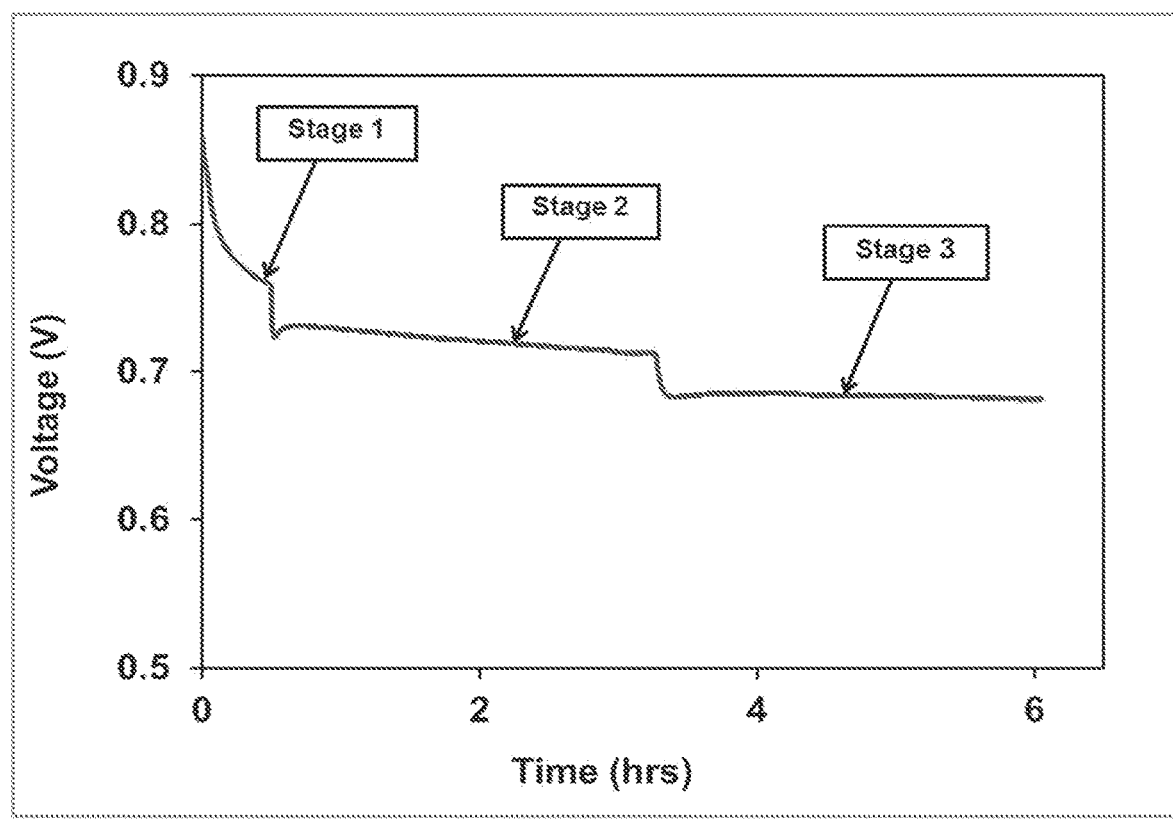
FIG. 10 is a graph illustrating steps of the nanowire growth in 3 stages.

To control the polymer growth, which ensures proper morphology and nanowire structure, the electrochemistry was carried out in three different stages as shown in FIG. 10. For the first stage, a constant current of 50 nA was applied for 30 minutes when the monomer was oxidized, and the seeding began.

The second and third stages each had duration of 2.8 hours. For the second stage, the current was held constant at 25 nA, and for the third stage the current was constant at 12.5 nA. The entire electro-polymerization process was conducted in ~6 hours. The low current ensured the nanoscale diameter of the polymer nanowires, a desirable feature for sensor chemistry. The device was then soaked in deionized (DI) water for ten minutes to remove any salt, and then dried overnight at 70° C. before imaging and characterizing the properties of the nanowires.

After the electro-polymerization process was completed, the polymer nanowires that formed were first characterized by generating a current-voltage (IV) curve of the device (a base line). Before electro-polymerization, the electrode junction device was an open circuit, and hence no current could flow through it. After electro-polymerization, when the nanowires had grown so as to bridge the 2 μm gap between the electrodes, resulting in a completed electrical circuit, the device recorded a current flowing across the gap. This enabled quick determination that the first step in the electrochemical process of forming a conductive bridge between the electrodes was successful. It was also evidenced that a high density of nanowires were formed in the 2 μm gap thus allowing a high current to flow through the nanowires because of a lowered resistance. If there was a low current measured, that low current evidenced a sparse growth of the nanofibers.

Figure 11A:
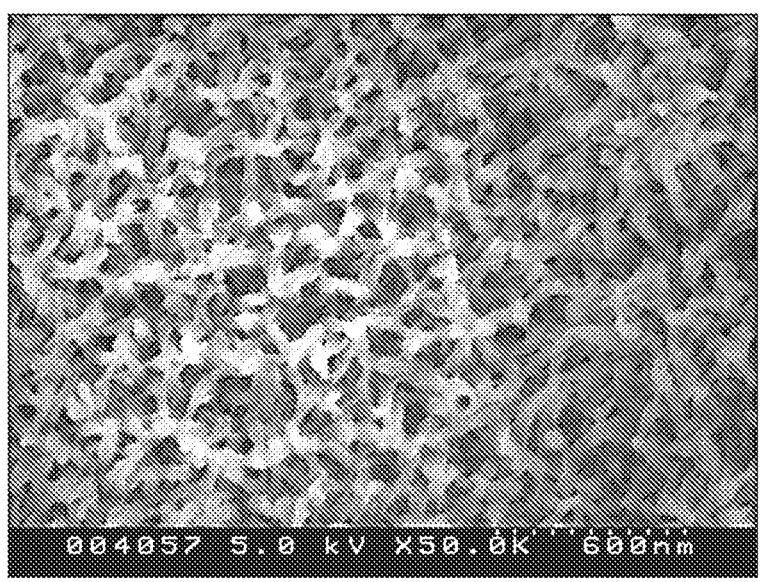
FIG. 11A is an SEM image of nanowires grown across the 2 µm gap between the electrodes.
Figure 11B:
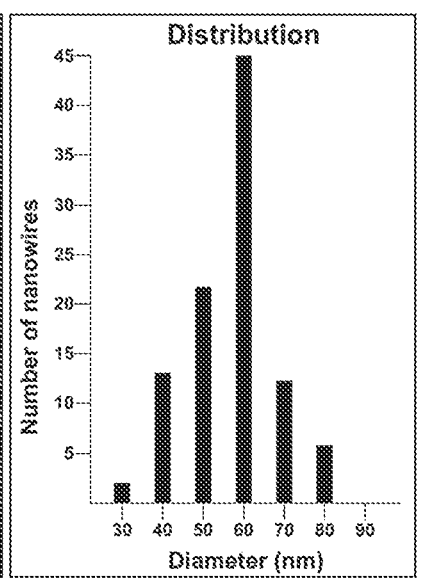
FIG. 11B is a graph illustrating the size distribution of nanowires illustrated in FIG. 11A.
Figure 12A:
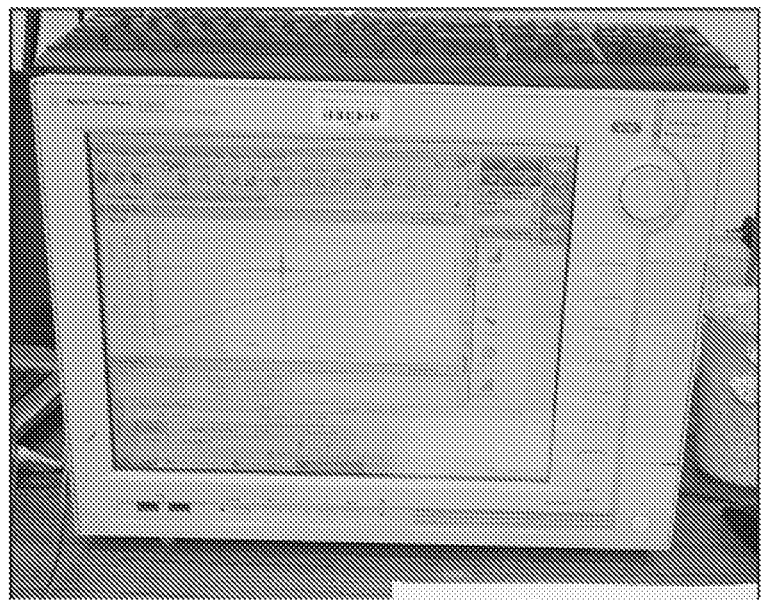
FIG. 12A is a photograph of an Agilent semi-conductor analyzer showing an I-V curve of nanowire grown devices.
Figure 12B:
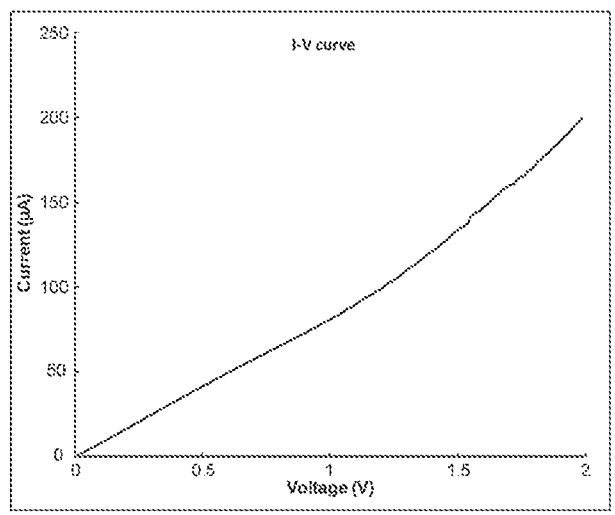
FIG. 12B is an enlarged view of the graph of the I-V curve shown on the analyzer.
Figures 14A, 14B:
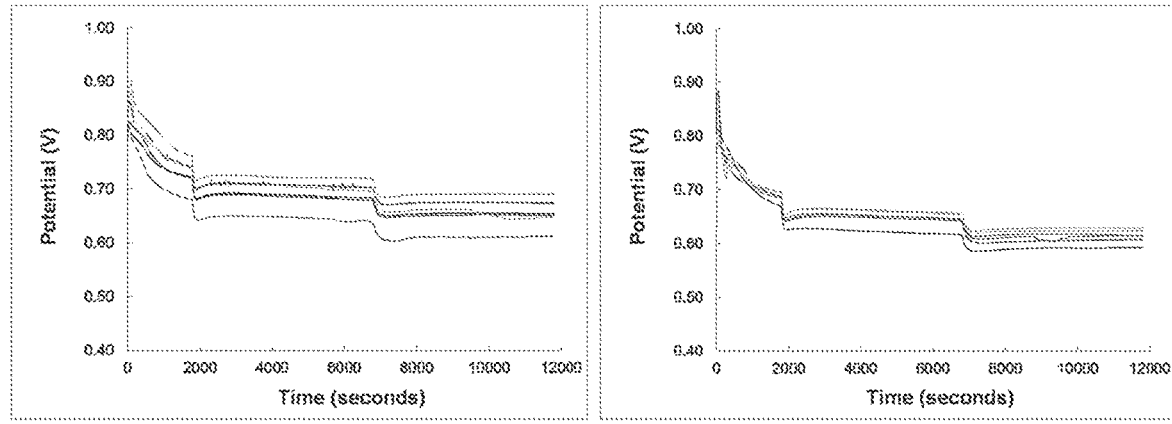
FIG. 14A is a graph of voltage-time(V-t) growth curves of six devices grown on a Princeton Applied Research model 263A-1 potentiostat/galvanostat.
FIG. 14B is a graph of voltage-time(V-t) growth curves of six devices grown on the CHI multiplexer instrument.
Figure 14C:
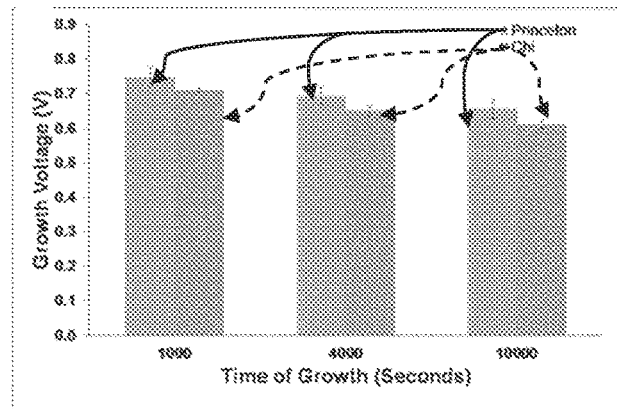
FIG. 14C is a graph comparing the average voltage of the device growth at 1000, 4000 and 10,000 seconds of growth for devices grown on the Princeton instrument compared to Devices grown on CHI instrument; N=6; Error bars–SD.
Figures 14D, 14E:
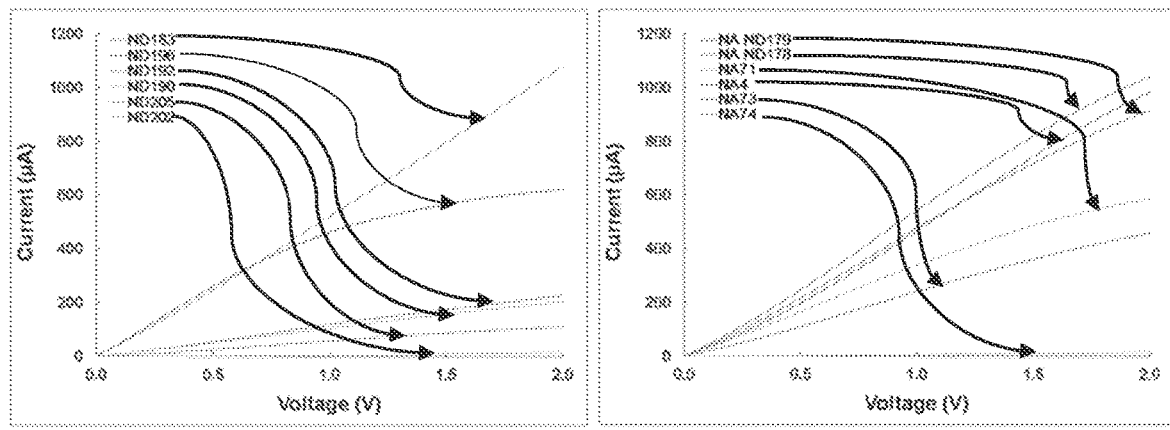
FIG. 14D is graph illustrating Current-Voltage (I-V) curves of devices grown on the Princeton instrument.
FIG. 14E is graph illustrating Current-Voltage (I-V) curves of devices grown on SIX the CHI multiplexer instrument.

High quality polymer nanowires (~50-150 nm diameter and >2 μm length) were successfully and consistently grown providing sensors with >85% reproducibility. The devices were characterized using SEM (see FIGS. 11A and 11B) and I-V measurements with an Agilentsemi-conductor analyzer shown in FIG. 12A. The histogram (FIG. 12B) derived from SEM images show that majority of the nanowires have a diameter of 60 nm which is within the desired range. The process of polymer growth was easily controlled by varying the concentration of the monomer used, reaction temperature, rate of polymerization, and applied potential.

Polymer Nanowire Growth Scale-Up Using Multiplexer

An enlarged electro-polymerization process, comprising a second electrochemical station supporting up to 24 channels is shown in FIGS. 13A-13D. This enabled up to 24 devices to be grown in series over a 72-hour period. Fabricating multiple devices at once reduces down time and overall setup time. After the electro-polymerization process was completed, the polymer nanowires grown using the multiplexer were characterized using the IV curve of the device as an operational base line for each of the nanowire chips. As shown in FIGS. 14A-14E, the growth curves (V-t) are consistent for both of the hardware platforms used for electro-polymerization of the sensor.

The different rates of growth resulted in different current ranges which can be used to sort out devices in different categories of current such as low, medium, and high current devices. Applicant's prior studies with the nanowire sensor have shown high current devices are not sensitive to analyte change and medium current devices perform better in terms of signal response due to change in analyte. These prior studies focused primarily on medium current devices (~200-800 μA) as starting materials to perform sensor evaluation.

Polymer Nanowire Functionalization

Polymer nanowires functionalized with engineered antibodies specific to ethylene receptors produce an electrical response to ethylene. Engineered antibodies and aptamers corresponding to ethylene receptors (ETR1, ETR2, ERS1 (ethylene response sensor 1), ERS2 and their isoforms and combinations thereof as described in Lacey (Lacey R F, Binder B M. "How Plants Sense Ethylene Gas—The Ethylene Receptors", *Journal of Inorganic Biochemistry.* 133 (2014) pp. 58-62) show sensitive and a high affinity response to ethylene.

Figure 15:
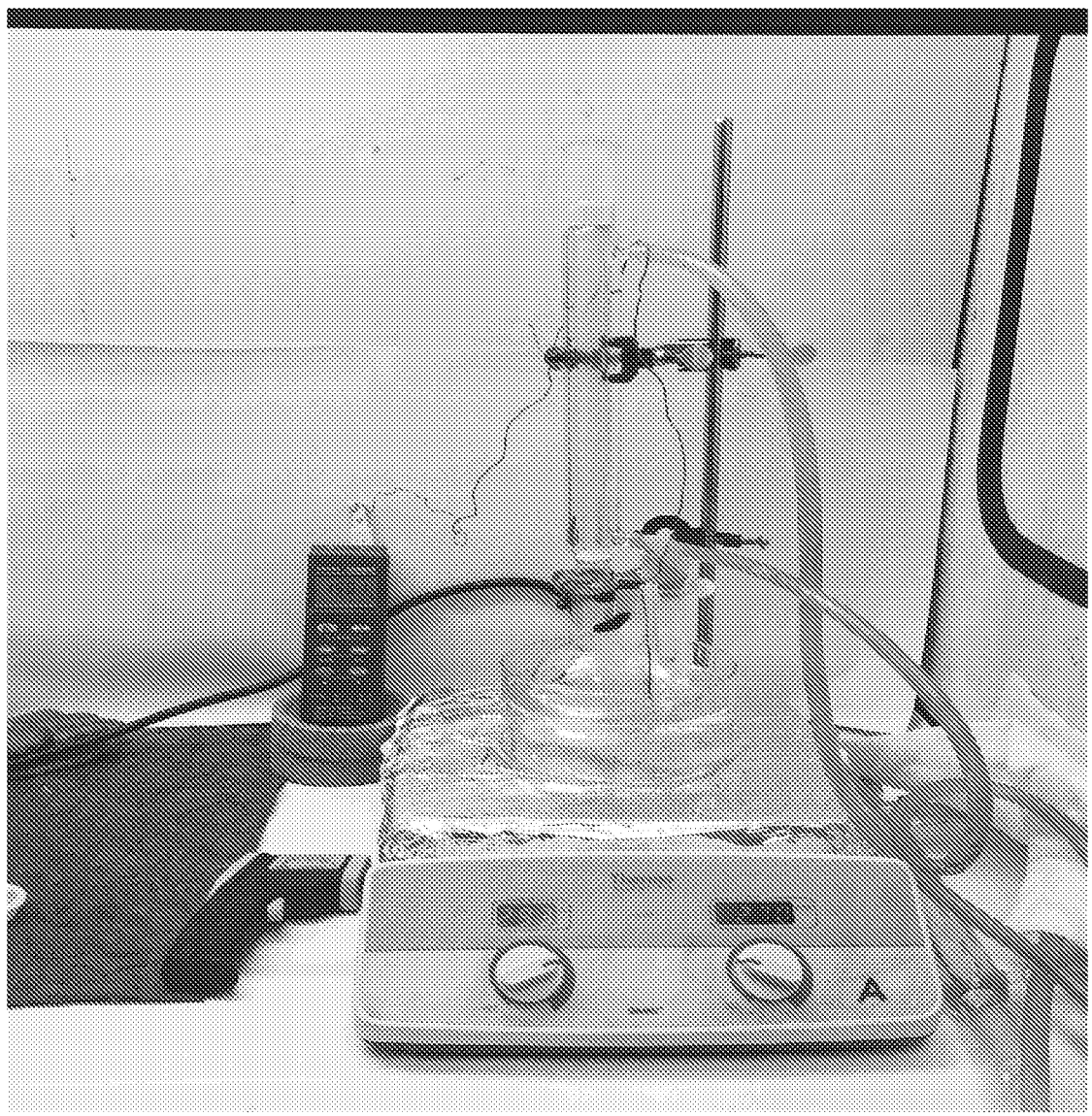
FIG. 15 is a photograph showing preparation of $Cu^I$ complex.
Figure 16:
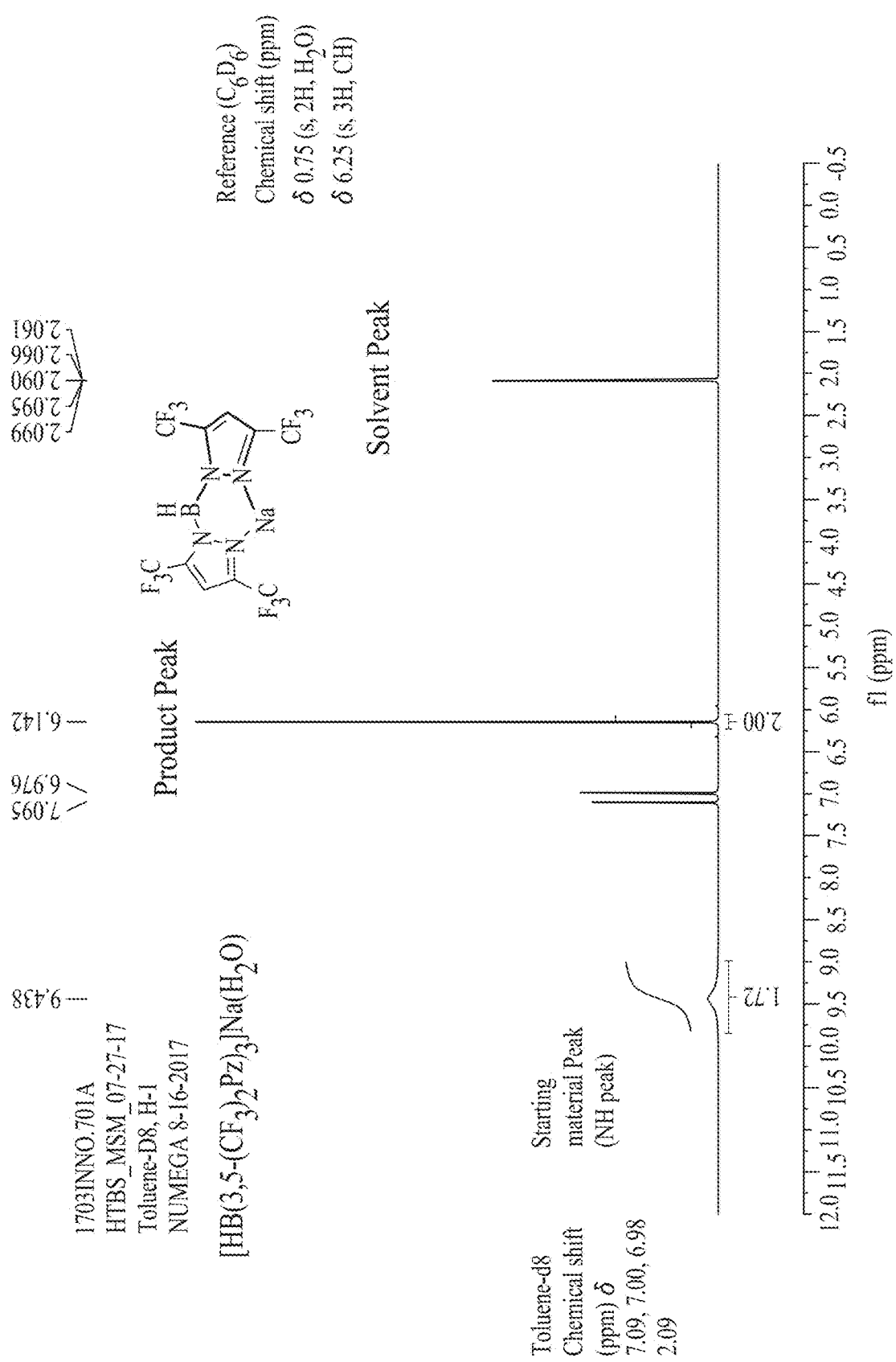
FIG. 16 shows the NMR spectra of Hydrotrix[3,5-bis(trifluoromethyl)-pyrazol-1-yl]borato sodium complex.
Figure 17:
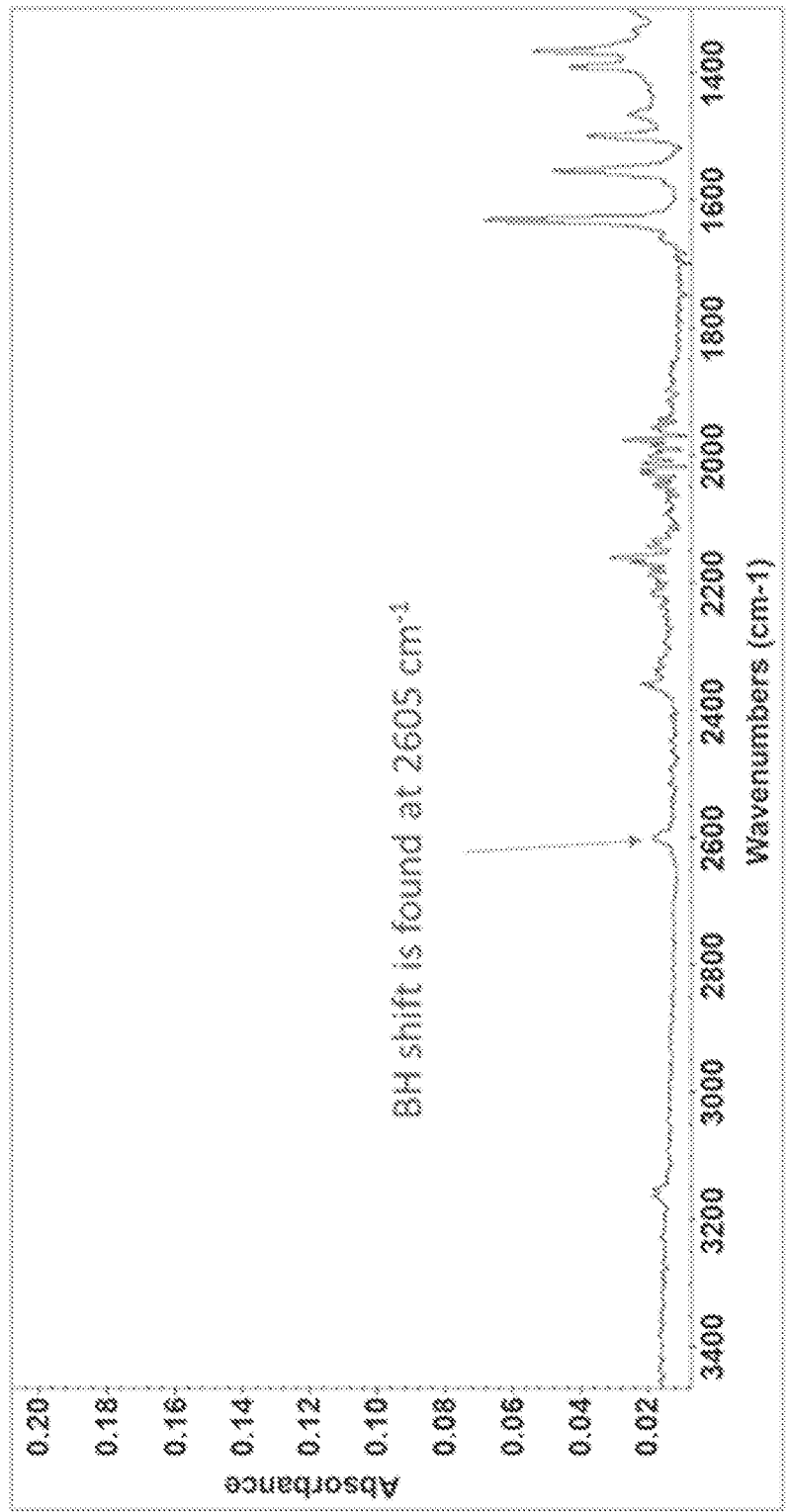
FIG. 17 is an FTIR spectra of Hydrotrix[3,5-bis(trifluoromethyl)-pyrazol-1-yl]borato sodium complex.

Hydrotris[3,5-bis(trifluoromethyl)-pyrazol-1-yl]borato sodium ($Na[HB(3,5-(CF_3)_2-Pz)_3]$) was synthesized using the procedure describe in US Published App. 2013/0273665A1 using the set up shown in FIG. 15 herein. NMR analysis confirmed the product peak (see FIG. 16) and FTIR spectra confirmed the characteristic boron hydride (BH) peak at 2400 cm-1 (FIG. 17). A CuI complex was then prepared based upon a fluorinated tris(pyrazolyl)borate ligand (Sigma), which interacts with the surface of polymer nanowires/SWNTs, thereby influencing their conductivity. Copper (I) triflate benzene complex $(CF_3SO_3Cu)_2 \cdot C_6H_6$ (8 mg, 15.9 mmol) was dissolved in dry, degassed toluene. Synthesized $Na[HB(3,5-(CF_3)_2-Pz)_3]$ complex was added, and the mixture was stirred for 14 hr. at room temperature followed by filtration to give a colorless solution. This solution was drop cast onto the nanowire/SWNT surface and allowed to dry at room temperature for 30 minutes followed by heating at 55° C. for 90 min to improve the contact between the nanomaterials and the copper ligand complex.

Figures 18, 19:
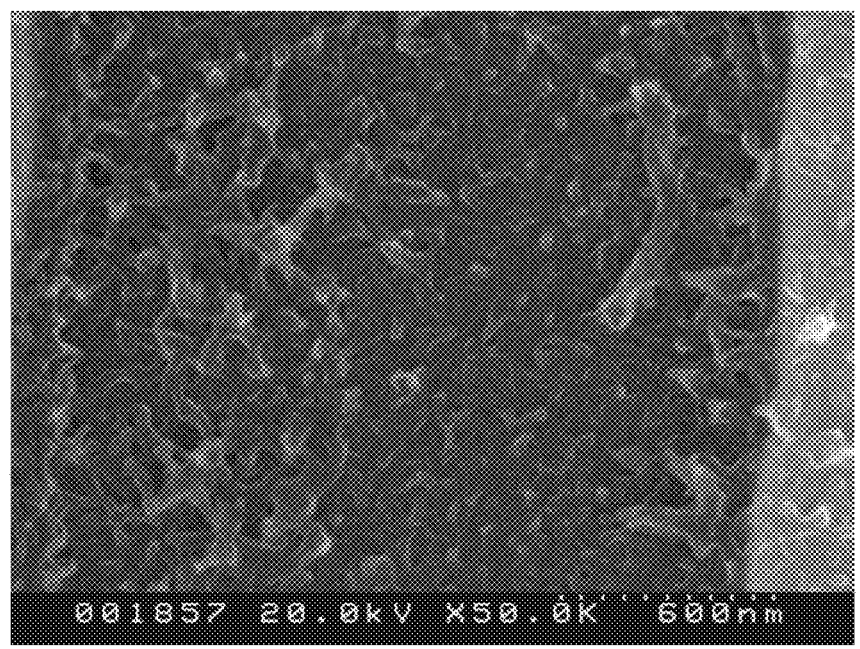
FIG. 18 is a table comparing theoretical vs. actual elemental analysis of Hydrotris[3,5-bis(trifluoromethyl)-pyrazol-1-yl]Borato Sodium Complex.
FIG. 19 is an SEM analysis of copper ligand functionalized devices.
Figure 20:
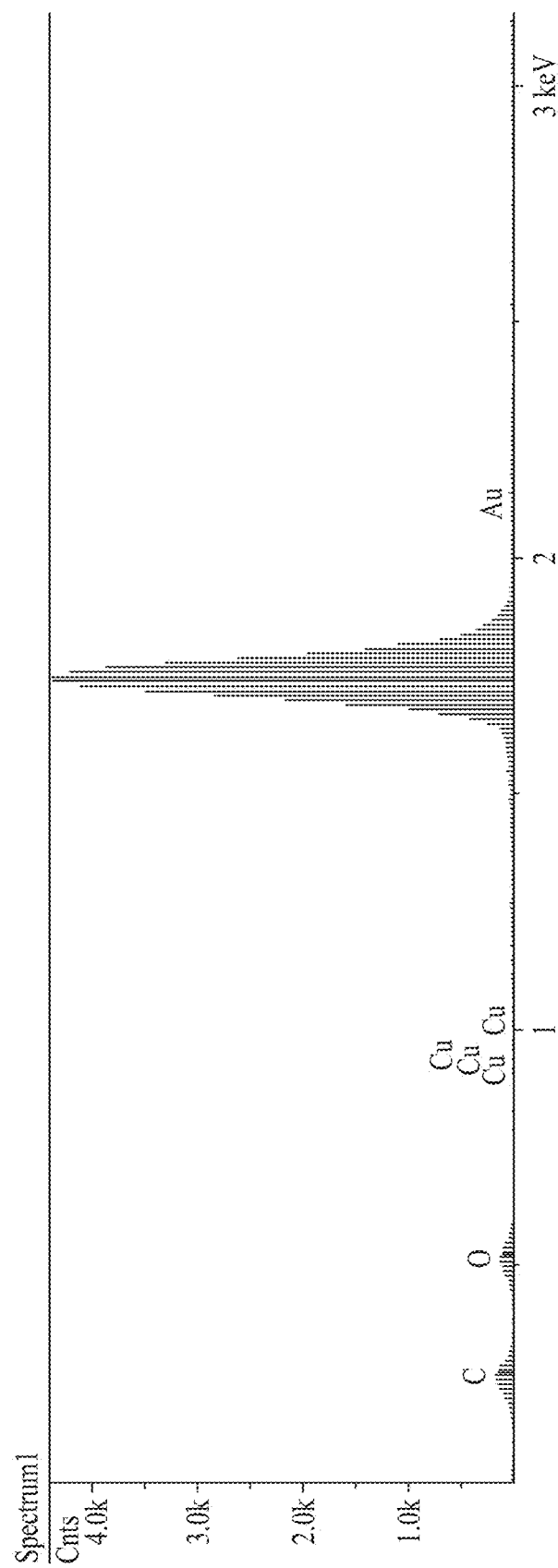
FIG. 20 is an EDS study showing the presence of copper on the surface of the nanowire grown devices.

Elemental analysis confirmed the composition of hydrotris[3,5-bis(trifluoromethyl)-pyrazol-1-yl]borato sodium which very closely matched the theoretical composition (See FIG. 18). An SEM image of a copper complexed device is shown in FIG. 19. Energy-dispersive X-ray spectroscopy (EDS) (FIG. 20) studies show the presence of copper on the surface of the nanowire grown devices which are masked due to the silicon peak.

Other commercially available copper complexes also found to be suitable for functionalizing the polymeric nanowires include 2-(1-Hydroxyethylidene)-1cyclopentanone-copper(II) complex

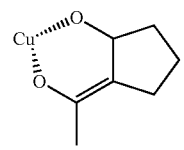

and copper(I)trifluoromethanesulphonate benzene complex.

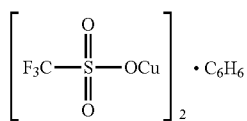

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to provide the desired features of the present invention. Also, a multitude of different constituent module names other than those depicted herein may be applied to the various components. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether flow control or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

We claim:

1. A system for receiving a gas steam from a gaseous environment for sensing the presence and concentration of ethylene in said gaseous environment, said system comprising:
   a. a chemical analysis section comprising an ethylene sensor, an ethylene scrubber, a $CO_2$ scrubber, gas flow control valves and a pump to feed quantities of the ethylene containing gaseous environment through the system, the chemical analysis section configured to alternatively deliver quantities of the gas stream in a measurement cycle or a recovery cycle,
   b. an electronics section comprising a power supply, a system control board and a measurement board, the measurement board receiving electrical signals from the ethylene sensor, c. the ethylene sensor comprising
  i. a substrate with two electrodes thereon, the electrodes separated by a gap of 0.5 to 4.0 µm, and
  ii. a nano-network of conductive polymer nanowires bridging the gap so as to provide an electrically conductive path between the electrodes, said nano-network exhibiting defined electrical characteristics,
  iii. the nanowires functionalized by application thereto of chemical compounds sensitive to the presence of ethylene, the electrical characteristics of the functionalized nanofibers changing in response to a defined quantities of ethylene in the gas stream fed to the ethylene sensor.

2. The system of claim 1 wherein the pump and gas flow valves are configured to alternatively deliver quantities of the gas stream to the ethylene scrubber during the recovery cycle or the ethylene sensor during the measurement cycle.

3. The system of claim 2 configured such that in the measurement cycle the gas stream flows from the gaseous environment into the pump, said pump delivering the gas stream to the $CO_2$ scrubber and then to the sensor cell, the sensor cell delivering an electrical signal to the system control board and a measurement board, said electrical signal indicating the ethylene concentration in the gas stream.

4. The system of claim 2 configured such that following completion of the measurement cycle the system enters a recovery cycle in which the valves switch the gas flow to direct the gas stream through the $CO_2$ and ethylene scrubbers while the resistance of the sensors cell is monitored by the measurement board, said recovery and scrubbing cycle continuing until the signal from the ethylene sensor fully returns to a base line status.

5. The system of claim 1 wherein the electrical signals from the ethylene sensor processed through the electronics section are displayed as showing ethylene concentrations from about 20 parts per billion up to at least about 100 parts per million.

6. The system of claim 1 wherein the conductive polymer nanofibers are functionalized with compounds chosen from the group consisting of copper complexes, engineered antibodies, peptide ligands, aptamers and combinations thereof.

* * * * *